US012565710B2

(12) United States Patent
Xu

(10) Patent No.: US 12,565,710 B2
(45) Date of Patent: *Mar. 3, 2026

(54) PHOTODEFINED APERTURE PLATE AND METHOD FOR PRODUCING THE SAME

(71) Applicant: Stamford Devices Limited, Dangan (IE)

(72) Inventor: Hong Xu, San Carlos, CA (US)

(73) Assignee: Stamford Devices Limited, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/411,467

(22) Filed: Jan. 12, 2024

(65) Prior Publication Data

US 2024/0344226 A1 Oct. 17, 2024

Related U.S. Application Data

(63) Continuation of application No. 17/808,432, filed on Jun. 23, 2022, now Pat. No. 11,905,615, which is a
(Continued)

(51) Int. Cl.
*C25D 7/00* (2006.01)
*A61M 11/00* (2006.01)
(Continued)

(52) U.S. Cl.
CPC ............ *C25D 7/00* (2013.01); *A61M 11/005* (2013.01); *B05B 17/0646* (2013.01);
(Continued)

(58) Field of Classification Search
CPC ..... B05B 17/0646; B41J 2/162; B41J 2/1625; B41J 2/1629; B41J 2/1631; C25D 7/00;
(Continued)

(56) References Cited

U.S. PATENT DOCUMENTS 2,266,706 A 12/1941 Fox et al.
3,130,487 A 4/1964 Mears
(Continued)

FOREIGN PATENT DOCUMENTS

CN 1149907 A 5/1997
DE 1948135 A1 4/1971
(Continued)

OTHER PUBLICATIONS

International Search Report and Written Opinion for corresponding International Application No. PCT/EP2011/067106, mailed May 8, 2012 (12 pages).
(Continued)

*Primary Examiner* — Steven J Ganey
(74) *Attorney, Agent, or Firm* — Bookoff McAndrews, PLLC

(57) ABSTRACT

In one embodiment, a method for manufacturing an aperture plate includes depositing a releasable seed layer above a substrate, applying a first patterned photolithography mask above the releasable seed layer, the first patterned photolithography mask having a negative pattern to a desired aperture pattern, electroplating a first material above the exposed portions of the releasable seed layer and defined by the first mask, applying a second photolithography mask above the first material, the second photolithography mask having a negative pattern to a first cavity, electroplating a second material above the exposed portions of the first material and defined by the second mask, removing both masks, and etching the releasable seed layer to release the first material and the second material. The first and second material form an aperture plate for use in aerosolizing a liquid. Other aperture plates and methods of producing aperture plates are described according to other embodiments.

19 Claims, 10 Drawing Sheets

Related U.S. Application Data continuation of application No. 16/852,692, filed on Apr. 20, 2020, now Pat. No. 11,389,601, which is a continuation of application No. 15/001,551, filed on Jan. 20, 2016, now Pat. No. 10,662,543, which is a continuation of application No. 13/976,628, filed as application No. PCT/US2011/067106 on Dec. 23, 2011, now Pat. No. 9,719,184.

(60) Provisional application No. 61/427,715, filed on Dec. 28, 2010.

(51) Int. Cl.

| | |
|---|---|
| *B05B 17/00* | (2006.01) |
| *B41J 2/16* | (2006.01) |
| *C25D 1/00* | (2006.01) |
| *C25D 3/38* | (2006.01) |
| *C25D 3/46* | (2006.01) |
| *C25D 3/48* | (2006.01) |
| *C25D 3/54* | (2006.01) |
| *C25D 5/00* | (2006.01) |
| *C25D 5/02* | (2006.01) |
| *C25D 5/10* | (2006.01) |
| *C25D 5/34* | (2006.01) |
| *C25D 5/48* | (2006.01) |
| *C25D 5/54* | (2006.01) |

(52) U.S. Cl.
CPC ............. *B41J 2/162* (2013.01); *B41J 2/1625* (2013.01); *B41J 2/1629* (2013.01); *B41J 2/1631* (2013.01); *C25D 1/003* (2013.01); *C25D 3/38* (2013.01); *C25D 3/46* (2013.01); *C25D 3/48* (2013.01); *C25D 3/54* (2013.01); *C25D 5/022* (2013.01); *C25D 5/10* (2013.01); *C25D 5/34* (2013.01); *C25D 5/48* (2013.01); *C25D 5/54* (2013.01); *C25D 5/611* (2020.08)

(58) Field of Classification Search
CPC . C25D 1/003; C25D 3/38; C25D 3/46; C25D 3/48; C25D 3/54; C25D 5/022; C25D 5/10; C25D 5/34; C25D 5/48; C25D 5/84
USPC ....... 239/548, 552, 596, 601, 533.12, 102.2; 205/75, 150; 347/47; 128/200.14, 128/200.16
See application file for complete search history.

(56) References Cited

U.S. PATENT DOCUMENTS

| | | | |
|---|---|---|---|
| 3,325,319 | A | 6/1967 | Frantzen |
| 4,184,925 | A | 1/1980 | Kenworthy |
| 4,246,076 | A | 1/1981 | Gardner |
| 4,264,714 | A | 4/1981 | Trausch |
| 4,374,707 | A | 2/1983 | Pollack |
| 4,379,737 | A | 4/1983 | Mearig |
| 4,430,784 | A | 2/1984 | Brooks et al. |
| 4,628,165 | A | 12/1986 | Nobel et al. |
| 4,773,791 | A | 9/1988 | Hartkorn |
| 4,839,001 | A | 6/1989 | Bakewell |
| 4,844,778 | A | 7/1989 | Witte |
| 4,849,303 | A | 7/1989 | Graham et al. |
| 4,972,204 | A | 11/1990 | Sexton |
| 5,152,456 | A | 10/1992 | Ross et al. |
| 5,164,740 | A | 11/1992 | Ivri |
| 5,167,776 | A | 12/1992 | Bhaskar et al. |
| 5,180,482 | A | 1/1993 | Abys et al. |
| 5,373,629 | A | 12/1994 | Hupe et al. |
| 5,443,713 | A | 8/1995 | Hindman |
| 5,487,378 | A | 1/1996 | Robertson et al. |
| 5,560,837 | A | 10/1996 | Trueba |
| 5,565,113 | A | 10/1996 | Hadimioglu et al. |

| | | | | |
|---|---|---|---|---|
| 5,586,550 | A | | 12/1996 | Ivri et al. |
| 5,646,662 | A | | 7/1997 | Kitahara |
| 5,685,491 | A | | 11/1997 | Marks et al. |
| 5,758,637 | A | | 6/1998 | Ivri et al. |
| 5,766,441 | A | | 6/1998 | Arndt et al. |
| 5,837,960 | A | | 11/1998 | Lewis et al. |
| 5,899,390 | A | | 5/1999 | Arndt et al. |
| 5,921,474 | A | | 7/1999 | Zimmermann et al. |
| 5,976,342 | A | | 11/1999 | Arndt et al. |
| 6,050,507 | A | | 4/2000 | Holzgrefe et al. |
| 6,074,543 | A | | 6/2000 | Yoshihira et al. |
| 6,170,763 | B1 | * | 1/2001 | Fuchs .................. F02M 61/186 239/596 |
| 6,205,999 | B1 | | 3/2001 | Ivri et al. |
| 6,230,992 | B1 | | 5/2001 | Arndt et al. |
| 6,235,177 | B1 | | 5/2001 | Borland et al. |
| 6,254,219 | B1 | * | 7/2001 | Agarwal ................ B41J 2/1603 347/65 |
| 6,310,641 | B1 | | 10/2001 | Mrvos et al. |
| 6,357,677 | B1 | | 3/2002 | Ren et al. |
| 6,371,596 | B1 | * | 4/2002 | Maze .................... B41J 2/1625 347/47 |
| 6,586,112 | B1 | | 7/2003 | Te |
| 6,605,866 | B1 | | 8/2003 | Crowley et al. |
| 6,773,094 | B2 | | 8/2004 | Linliu et al. |
| 7,066,398 | B2 | | 6/2006 | Borland et al. |
| 7,104,475 | B2 | | 9/2006 | Goenka et al. |
| 7,259,640 | B2 | | 8/2007 | Brown et al. |
| 7,442,303 | B2 | | 10/2008 | Jacobson |
| 8,398,001 | B2 | | 3/2013 | Borland et al. |
| 9,719,184 | B2 | | 8/2017 | Xu |
| 10,508,353 | B2 | | 12/2019 | Xu |
| 10,662,543 | B2 | * | 5/2020 | Xu .......................... C25D 3/38 |
| 2001/0013554 | A1 | | 8/2001 | Borland et al. |
| 2002/0063751 | A1 | | 5/2002 | Aizawa et al. |
| 2002/0157956 | A1 | | 10/2002 | Ikeda |
| 2003/0231227 | A1 | | 12/2003 | Kim |
| 2004/0035413 | A1 | | 2/2004 | Smaldone et al. |
| 2005/0263608 | A1 | | 12/2005 | Ivri |
| 2006/0055739 | A1 | | 3/2006 | Kim et al. |
| 2006/0086689 | A1 | | 4/2006 | Raju |
| 2006/0203036 | A1 | | 9/2006 | Sexton et al. |
| 2007/0023547 | A1 | | 2/2007 | Borland et al. |
| 2007/0212653 | A1 | | 9/2007 | Hori |
| 2007/0277816 | A1 | | 12/2007 | Morrison et al. |
| 2008/0023572 | A1 | | 1/2008 | Clark |
| 2009/0053174 | A1 | | 2/2009 | Kaneko et al. |
| 2010/0055045 | A1 | | 3/2010 | Gerhart et al. |
| 2010/0282247 | A1 | | 11/2010 | Kadrichu et al. |
| 2010/0319694 | A1 | | 12/2010 | Cook et al. |
| 2013/0252020 | A1 | | 9/2013 | Hradil |
| 2013/0334338 | A1 | | 12/2013 | Hogan |
| 2013/0334339 | A1 | | 12/2013 | Xu |
| 2015/0101596 | A1 | | 4/2015 | Hogan |
| 2015/0336115 | A1 | | 11/2015 | Hogan et al. |

FOREIGN PATENT DOCUMENTS

| | | | |
|---|---|---|---|
| DE | 2050285 | A1 | 5/1972 |
| DE | 19527846 | A1 | 1/1997 |
| EP | 0683048 | A2 | 11/1995 |
| EP | 1027993 | A1 | 8/2000 |
| EP | 1199382 | A1 | 4/2002 |
| EP | 1810743 | A1 | 7/2007 |
| EP | 2204238 | A1 | 7/2010 |
| GB | 2240494 | A | 8/1991 |
| GB | 2524337 | A | 9/2015 |
| JP | 4183892 | A1 | 6/1992 |
| JP | H04322290 | A | 11/1992 |
| JP | H05239682 | A | 9/1993 |
| JP | H0574669 | U | 10/1993 |
| JP | H0682583 | A | 3/1994 |
| JP | 7329304 | | 12/1995 |
| JP | H0839548 | A | 2/1996 |
| JP | H10507243 | A | 7/1998 |
| JP | H10228114 | A | 8/1998 |
| JP | 11138827 | | 5/1999 |
| JP | 2001200420 | A | 7/2001 |
| JP | 2002019125 | A | 1/2002 |

(56) References Cited

FOREIGN PATENT DOCUMENTS

| | | | |
|---|---|---|---|
| JP | 2002166541 | A | 6/2002 |
| JP | 2002187374 | A | 7/2002 |
| JP | 2002289097 | A | 10/2002 |
| JP | 2004223842 | A | 8/2004 |
| JP | 2004290426 | A | 10/2004 |
| JP | 2006056151 | A | 3/2006 |
| JP | 20060297688 | A | 11/2006 |
| JP | 2008545525 | A | 12/2008 |
| JP | 2009195669 | A | 9/2009 |
| JP | 2010540526 | A | 12/2010 |
| RU | 2078405 | C1 | 4/1997 |
| WO | 9103920 | A2 | 3/1991 |
| WO | 0118280 | A1 | 3/2001 |
| WO | 01071065 | | 3/2001 |
| WO | 2006127181 | A2 | 11/2006 |
| WO | 2009042187 | A1 | 4/2009 |
| WO | 2010134967 | A1 | 11/2010 |
| WO | 2011039233 | A1 | 4/2011 |
| WO | 2011083380 | A1 | 7/2011 |
| WO | 2011139233 | A1 | 11/2011 |
| WO | 2012092163 | A1 | 7/2012 |
| WO | 2013186031 | A2 | 12/2013 |

OTHER PUBLICATIONS

Lu, et al., "Grain Refinement in the Solidification of Undercooled Ni—Pd Alloys," Journal of Crystal Growth, 309, 2007 (9 pages).
Search Report by Registered Search Organization for Japanese Patent Application No. 2013-54784 dated Nov. 9, 2015 with English Translation (37 pages).
Search Report from Chinese Patent Application No. 2011800685681 dated Oct. 30, 2014 (1 page).
Supplementary Search Report from Chinese Patent Application No. 2011800685681 dated Jul. 3, 2015 (1 page).
Vecellio, L., "The mesh nebulizer: a recent innovation for aerosol delivery," Breathe, vol. 2, No. 3, Mar. 2006 (10 pages).

* cited by examiner

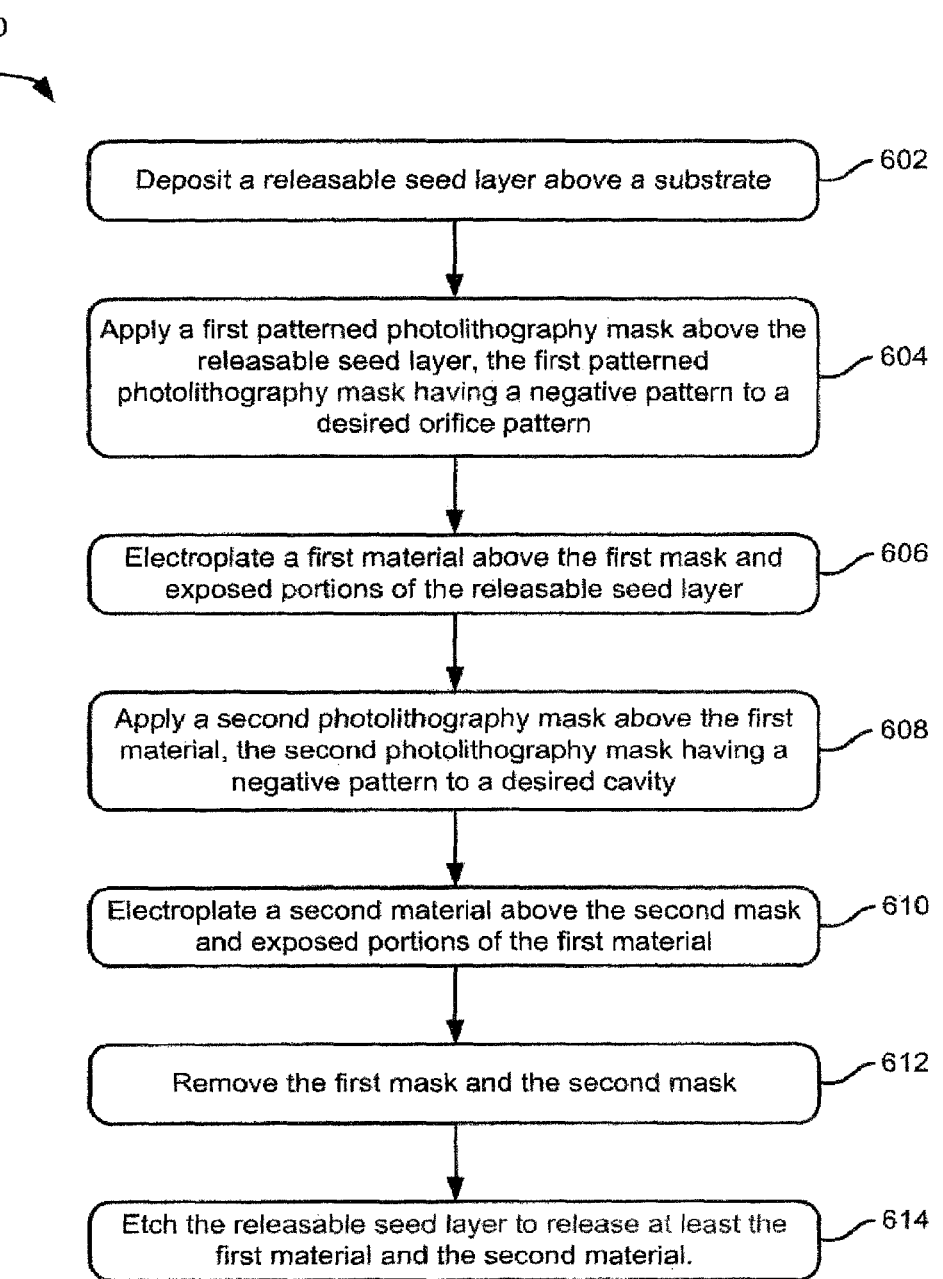

600

Deposit a releasable seed layer above a substrate — 602

Apply a first patterned photolithography mask above the releasable seed layer, the first patterned photolithography mask having a negative pattern to a desired orifice pattern — 604

Electroplate a first material above the first mask and exposed portions of the releasable seed layer — 606

Apply a second photolithography mask above the first material, the second photolithography mask having a negative pattern to a desired cavity — 608

Electroplate a second material above the second mask and exposed portions of the first material — 610

Remove the first mask and the second mask — 612

Etch the releasable seed layer to release at least the first material and the second material. — 614

FIG. 6

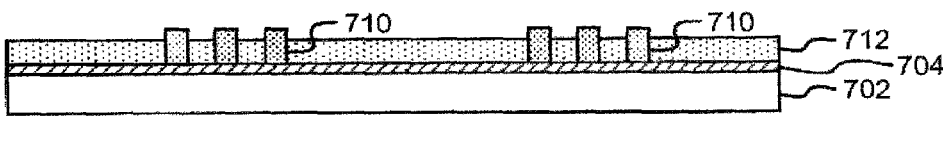
FIG. 7F
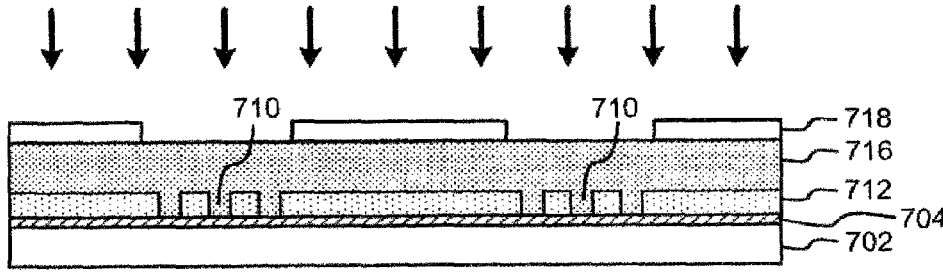
FIG. 7G
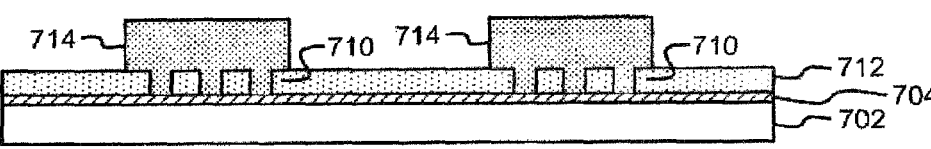
FIG. 7H
FIG. 7I

PHOTODEFINED APERTURE PLATE AND METHOD FOR PRODUCING THE SAME

CROSS-REFERENCE TO RELATED APPLICATION(S)

This patent application is a continuation of U.S. application Ser. No. 17/808,432, filed Jun. 23, 2022, which is a continuation of U.S. Application Ser. No. 16/852,692, filed Apr. 20, 2020, now U.S. Pat. No. 11,389,601, which is a continuation of U.S. application Ser. No. 15/001,551, filed Jan. 20, 2016, now U.S. Pat. No. 10,662,543, which is a continuation of U.S. application Ser. No. 13/976,628, filed Sep. 9, 2013, now U.S. Pat. No. 9,719,184, which is a § 371 national entry of International Application No. PCT/US2011/067106, filed Dec. 23, 2011, which claims the benefit of priority to U.S. Provisional Application No. 61/427,715, filed on Dec. 28, 2010, all of which are incorporated herein by reference in their entireties.

FIELD OF THE INVENTION

The present invention relates to liquid nebulizers, and more particularly, to an aperture plate for such liquid nebulizers capable of aerosol delivery of liquid formulations having a controlled liquid droplet size suitable for pulmonary drug delivery. The invention further relates to the formation and use of aperture plates employed to produce such aerosols.

BACKGROUND

In drug delivery applications, especially drug delivery to the pulmonary system of a patient, liquid nebulizers are advantageous in that they are capable of delivering a fine mist of aerosol to a patient. A goal of such nebulizer devices is to assure a consistent droplet size and/or flow rate and/or velocity of the expelled droplets to maximize delivery to the targeted portion of the pulmonary system, such as the deep lung.

Some liquid nebulizers use a perforated plate, such as an aperture plate (AP), mesh plate, or vibrating plate, through which a liquid is forced in order to deliver a fine mist of aerosol. In particular, vibrating mesh-type liquid nebulizers are advantageous over other types of aerosolization devices, such as jet nebulizers or ultrasound nebulizers, in that they are capable of delivering a fine aerosol mist comprising a droplet size and droplet size range appropriate for pulmonary delivery, and can do so with relatively high efficiency and reliability. Such vibrating mesh nebulizers can be advantageously small, do not require large and/or external power sources, and do not introduce extraneous gases into a patient's pulmonary system.

Aperture plates manufactured for liquid drug pulmonary delivery are often designed to have apertures sized to produce droplets (also sometimes referred to as particles) of a size range from about 1-6 μm. Conveniently, the aperture plate may be provided with at least about 1,000 apertures so that a volume of liquid in a range from about 4-30 μL may be produced within a time of less than about one second. In this way, a sufficient dosage may be aerosolized. An aperture size of the aperture plate of about 1-6 μm is useful because this particle size range provides a deposition profile of aerosol droplets into the pulmonary system. More particularly, a size range of about 1-4 μm is useful because this particle size range provides a deposition profile of aerosol droplets into the deep lung (comprising the bronchi and bronchioles, and sometimes referred to as the pulmonary region), with a higher effective dose delivered, and concomitant therapeutic benefits. A particle size range larger than about 6 μm may decrease appropriate dispersal of the liquid into the pulmonary region of the lung. Therefore, providing an appropriate aperture size range, and controlling the aperture size distribution, and thereby the size distribution of liquid droplets, is a concern in this industry. Development of a cost-efficient manufacturing process to consistently and reliably manufacture aperture plates having the appropriate aperture sizes has been a challenge for the electroforming technology typically used to produce aperture plates.

Electroforming is a well established plating technology as it has been widely used in the inkjet printer industry. Such devices typically have large geometry apertures (about 10 μm or larger, in some examples). In a typical electroforming process, a metal forming process is used to form thin parts through electrodeposition onto a base form, referred to as a mandrel. In a basic electroforming process, an electrolytic bath is used to deposit an electroplatable metal onto a patterned conductive surface, such as metalized (i.e., deposited with a thin layer of metal) glass or stainless steel. Once the plated material has been built up to a desired thickness, the electroformed part is stripped off the master substrate. This process affords adequate reproducibility of the master and therefore permits production with good repeatability and process control for larger geometry (greater than about 10 μm) apertures. The mandrel is usually made of a conductive material, such as stainless steel. The object being electroformed may be a permanent part of the end product or may be temporary, and removed later, leaving only the metal form, i.e., "the electroform".

The electroforming process is, however, disadvantageous in many respects. Electroforming is very susceptible to imperfections, and defects at a mandrel surface (e.g., a supporting substrate surface) adversely affect the quality of a resultant aperture plate. As a result, high manufacturing yield and process consistency has remained elusive. A typical aperture plate manufacturing yield is about 30%, and a 100% downstream assembly line inspection may be required because of process variability.

A cross-sectional view of an electroformed aperture plate and a typical process flow are shown in FIG. 1A and FIG. 1B, respectively, according to the prior art. Conventionally, as shown in FIG. 1A, an aperture plate 102 is formed through three-dimensional growth of plating material on an array of dome-shaped patterns 104 with a specific diameter and spacing. The dome pattern 104 is lithographically patterned, and then heat treated on a stainless steel mandrel. The dome-shaped structure 104 acts only as an insulating layer for subsequent plating, precluding accurate and precise control of aperture geometry. The diameter and height of the dome-shaped structure 104 determines the approximate aperture 106 size and shape of aperture plates 102 produced through this process. The spacing or pitch between the dome-shaped structures 104 is a factor in determining the final aperture plate 102 thickness because the aperture 106 size is determined by the plating time, that is, a longer plating time results in a smaller aperture 106 size. As a result, the aperture plate hole density for a conventional, electroformed aperture plate 102 is fixed for any given plate thickness. Because flow rate is proportional to the aperture plate aperture (or hole) density, the hole density limitation of electroforming requires increasing the diameter of the aperture plate in order to deliver a higher flow rate. By "aperture density" it is meant the number of apertures per square unit of aperture plate, such as the number of apertures per $mm^2$. This has a significantly negative impact on manufacturing costs and manufacturing yield, e.g., the costs may be higher and yields may be lower. Moreover, particularly in medical applications, it is often preferable to minimize the diameter of an aperture plate so that the entire device is as small as possible, both for positioning and space requirements, and to minimize power consumption.

Another limiting factor with the prior art electroforming process is aperture size control. As shown in FIGS. 2A-2D, to achieve a smaller aperture 202, the risk of aperture plate hole blockage increases greatly (due to a diffusion limiting factor near the tapered aperture area). The three-dimensional growth has both a linear horizontal growth TH and a linear vertical growth $r_L$. At a large aperture 202 size (typically greater than about 10 μm), there is approximately a linear relationship between the horizontal growth TH and the vertical growth $r_L$ which allows for the aperture 202 size to be relatively well controlled. However, once the aperture 202 size reaches a smaller dimension, the linearity no longer holds, and controlling the aperture 202 size becomes difficult. This non-linearity typically starts at aperture sizes of about 10 μm or smaller, such as smaller than about 9 μm or 8 μm or 7 μm or 6 μm. As can be seen in FIGS. 2A-2D, the longer the growth time, as indicated by the time (t) values in each figure, the thicker the layer 204 becomes and the smaller the corresponding aperture 202 becomes. Because the thickness 204 and aperture 202 size are interrelated during the three-dimensional growth, plating conditions must be monitored and modified during the plating process if the final desired aperture 202 size is to be achieved, and this is not always successful. In some cases, as shown in FIG. 2D, the growth of the aperture plate may fail due to the layer being overgrown which causes the apertures 202 to close. It is well known in the art that plating thickness 204 can fluctuate, sometimes by over 10%, across the plating layer due to inherent limits of this process technology. Again, this makes it very difficult to control both the final aperture plate thickness 204 and aperture 202 size.

SUMMARY

According to one or more embodiments, a method for manufacturing an aperture plate includes depositing a releasable seed layer above a substrate, applying a first patterned photolithography mask above the releasable seed layer, the first patterned photolithography mask having a negative pattern to a desired aperture pattern, electroplating a first material above the exposed portions of the releasable seed layer and defined by the first mask, applying a second photolithography mask above the first material, the second photolithography mask having a negative pattern to a first cavity, electroplating a second material above the exposed portions of the first material and defined by the second mask, removing both masks, and etching the releasable seed layer to release the first material and the second material. The first material and the second material form an aperture plate for use in aerosolizing a liquid.

According to another embodiment, an aperture plate for use in aerosolizing a liquid includes a first material having a plurality of apertures therein, the first material having a characteristic of being formed through a photolithography process, a second material above the first material, the second material having a first cavity above the plurality of apertures in the first material, wherein the second material has a characteristic of being formed through a photolithography process. The first material and the second material form an aperture plate.

In yet another embodiment, an aperture plate adapted for use in aerosolizing a liquid produced by a process which includes the steps of: a) depositing a releasable seed layer above a substrate, b) applying a first patterned photolithography mask above the releasable seed layer, the first patterned photolithography mask having a negative pattern to a desired aperture pattern, c) electroplating a first material above the exposed portions of the releasable seed layer and defined by the first mask to form a substantially planar structure having a plurality of apertures therethrough, d) applying a second photolithography mask above the first material, the second photolithography mask having a negative pattern to a first cavity, wherein the first cavity is positioned above the plurality of apertures, e) electroplating a second material above the exposed portions of the first material and defined by the second mask, f) removing both masks, and g) etching the releasable seed layer to release the first material and the second material.

Other aspects and embodiments of the present invention will become apparent from the following detailed description, which, when taken in conjunction with the drawings, illustrate by way of example the principles of the invention.

BRIEF DESCRIPTION OF THE DRAWINGS

FIG. 6 shows a flowchart of a method of producing an aperture plate according to one embodiment.

FIGS. 7A-7L show various stages of formation of an aperture plate according to one embodiment.

DETAILED DESCRIPTION

Figure 1A:
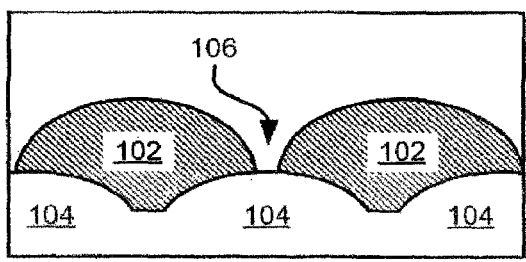
FIG. 1A shows a profile schematic of an aperture plate according to the prior art.
Figure 1B:
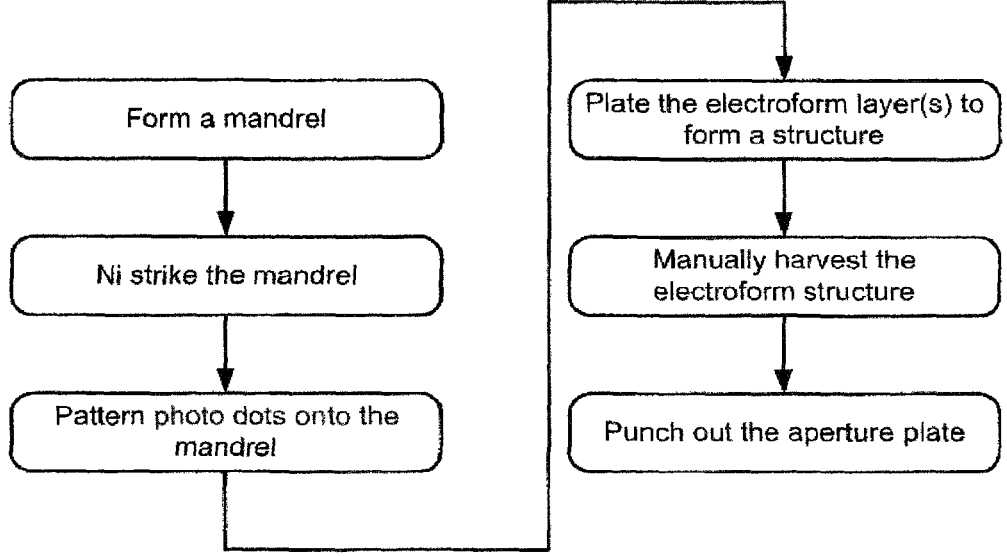
FIG. 1B shows a flowchart of a method of producing an aperture plate according to the prior art.
Figures 2A, 2B, 2C, 2D:
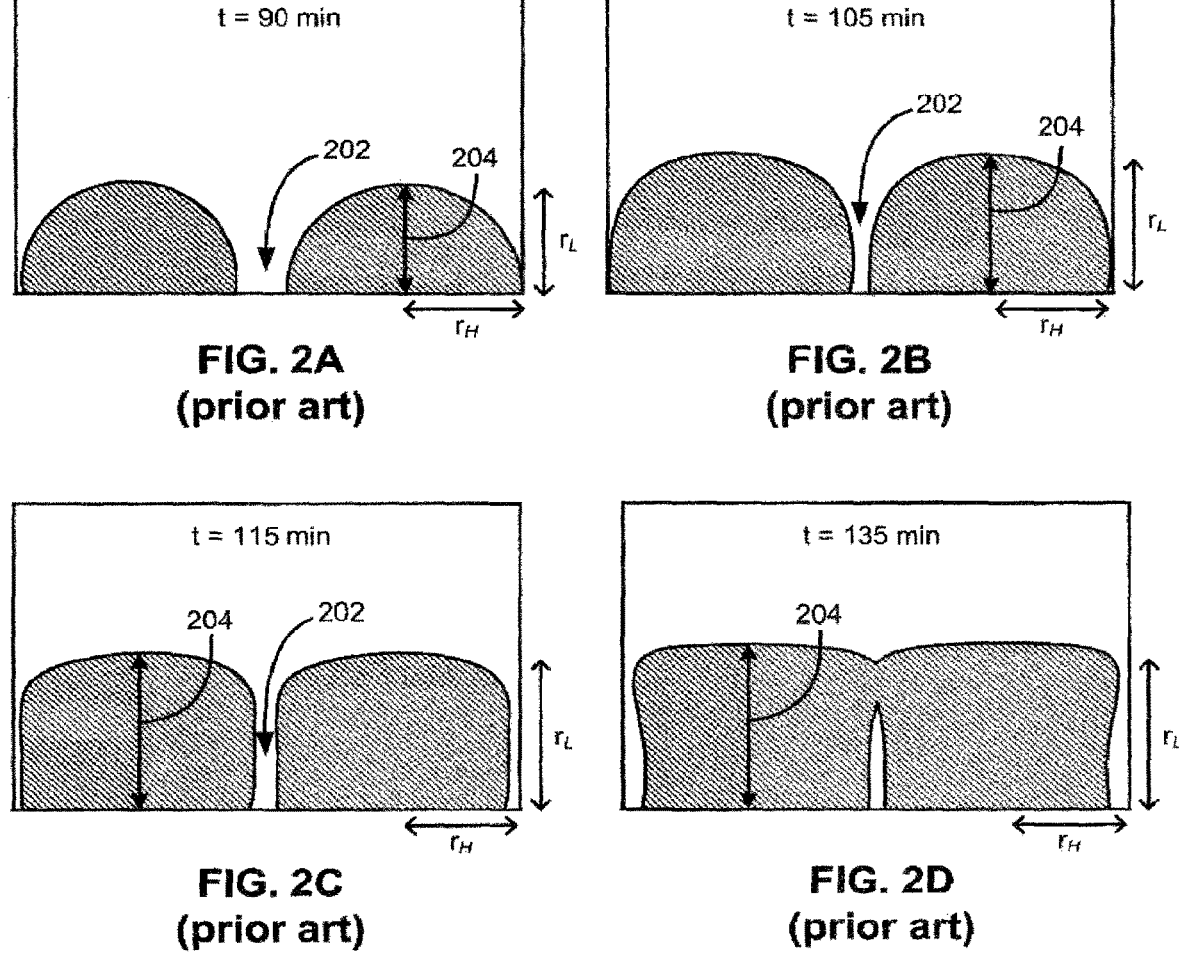
FIGS. 2A-2D show profile schematics during various stages of aperture plate growth, according to the prior art.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

As used herein, the term "liquid" may refer to a single phase solution, a multiple phase solution, an emulsion or nanosuspension.

As used herein the term "cylinder" (and "cylindrical") refer to a geometric figure comprising a section of a right circular cylinder; however, unless clear from the context, other cross sectional shapes may comprise the cylinders referred to herein. Moreover, the radius of the cylinder does not necessarily have to be uniform throughout the cylindrical shape, but may, in some embodiments, vary such as from top to bottom to result in some degree of taper.

It must also be noted that, as used in the specification and the appended claims, the singular forms "a," "an" and "the" include plural unless otherwise specified.

According to one general embodiment, a method for manufacturing an aperture plate includes depositing a releasable seed layer above a substrate, applying a first patterned photolithography mask above the releasable seed layer, the first patterned photolithography mask having a negative pattern to a desired aperture pattern, electroplating a first material above the exposed portions of the releasable seed layer and defined by the first mask, applying a second photolithography mask above the first material, the second photolithography mask having a negative pattern to a first cavity, electroplating a second material above the exposed portions of the first material and defined by the second mask, removing both masks, and etching the releasable seed layer to release the first material and the second material. The first material and the second material form an aperture plate for use in aerosolizing a liquid.

According to another general embodiment, an aperture plate for use in aerosolizing a liquid includes a first material having a plurality of apertures therein, the first material having a characteristic of being formed through a photolithography process, a second material above the first material, the second material having a first cavity above the plurality of apertures in the first material, wherein the second material has a characteristic of being formed through a photolithography process. The first material and the second material form an aperture plate.

In yet another general embodiment, an aperture plate adapted for use in aerosolizing a liquid produced by a process which includes the steps of: a) depositing a releasable seed layer above a substrate, b) applying a first patterned photolithography mask above the releasable seed layer, the first patterned photolithography mask having a negative pattern to a desired aperture pattern, c) electroplating a first material above the exposed portions of the releasable seed layer and defined by the first mask to form a substantially planar structure having a plurality of apertures therethrough, d) applying a second photolithography mask above the first material, the second photolithography mask having a negative pattern to a first cavity, wherein the first cavity is positioned above the plurality of apertures, e) electroplating a second material above the exposed portions of the first material and defined by the second mask, f) removing both masks, and g) etching the releasable seed layer to release the first material and the second material.

According to one or more embodiments, a process for making aperture plates with a precisely defined aperture size and shape to meet a specified droplet size and droplet size distribution is presented. Moreover, the photo-defined approach of the present invention permits decoupling of flow rate from the droplet size and/or size distribution.

Hence, the present invention allows for aperture plate production wherein flow rate and droplet size and/or size distribution may be addressed and controlled independently of one another, which is another significant advantage over the prior art. In addition, embodiments described herein provide scalability capable of large-volume manufacturing by removing costly, labor-intensive manual process steps (e.g., manual harvesting and punching) from the manufacturing processes. Prior art methods use a manual process named "harvesting" to peel a final plated material off a supporting substrate (e.g., mandrel) and then punch sheet material into a desired diameter to be used as aperture plates.

According to one or more embodiments, a method for manufacturing an aperture plate, mesh, perforated plate, etc., for a liquid nebulizer, such as a vibrating mesh nebulizer comprises a photolithography process, which affords precise aperture size definition and control. This photolithography method of making aperture plates may, in one or more embodiments, provide a parametrically-controlled aperture plate to meet desired specifications for delivery of a wide variety of liquid delivery applications, such as delivery of aerosolized drug formulations. Furthermore, the photo-defined process has a significant potential to markedly improve process yield and thus offers a significant potential to lower manufacturing cost.

According to some embodiments, semiconductor process techniques may be applied to the method of manufacturing of the present invention to enable a fully automatable process flow for the manufacturing of aperture plates through photomask design. Also, instead of being limited to stainless steel substrates, a more conventional silicon wafer may be used, along with a convenient release process utilizing a release layer and an etching process to remove the release layer, such as a wet etching release process.

Figure 3A:
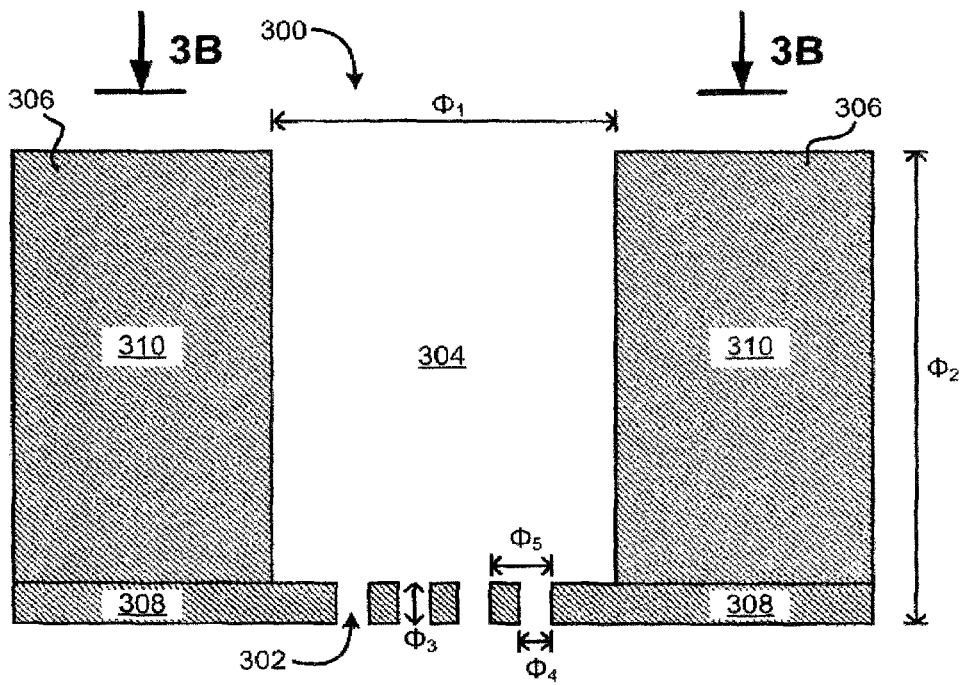
FIGS. 3A-3B show a cross-sectional view and a top view, respectively, of an aperture plate, according to one embodiment.
Figure 3B:
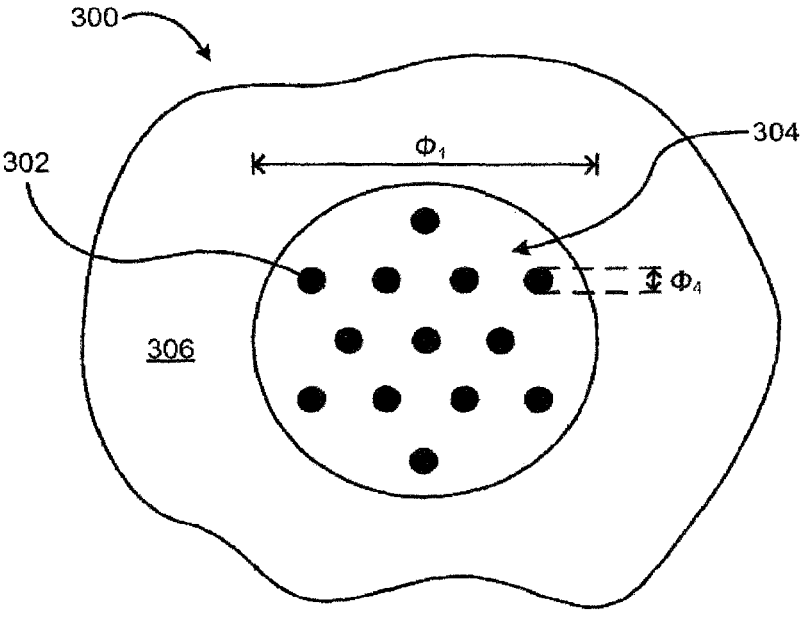

Now referring to FIGS. 3A-3B, a cross-sectional view and top view of an aperture plate 300 formed through a photolithography process are shown according to one embodiment. As can be seen in FIG. 3A, the aperture plate 300 includes a plurality of apertures 302, a cavity 304, and sidewalls 306. The aperture plate 300 is used for aerosolizing a liquid, according to preferred embodiments. The aperture plate 300 comprises a first material 308 having a plurality of apertures 302 therein. The first material 308 is a layer having a thickness $\Phi_3$ the same as a height of the apertures 302. The first material 308 has one or more characteristics resulting from formation through a photolithography process, such as a smooth surface, well controlled diameters ($\Phi_1$, $\Phi_4$) and pitch ($\Phi_5$), uniform dimensions, etc. The aperture plate 300 also comprises a second material 310 (which may comprise the same material or a different material than the first material 308) which is positioned directly or indirectly above the first material 308, such that the first material 308 may form the apertures 302 and the second material 310 may define the cavity 304 and form the sidewalls 306. The cavity 304 defined by the second material 310 is positioned above the plurality of apertures 302 in the first material 308. The second material 310 is a layer having a thickness the same as a depth of the cavity 304, e.g., $\Phi_2$-$\Phi_3$. The second material 310 also has one or more characteristics resulting from formation through a photolithography process, as described previously.

In one approach, each of the plurality of apertures 302 of the first material 308 may have a diameter $\Phi_4$ of between about 1 μm and about 5 μm. In another approach, a thickness $\Phi_3$ of the first material 308 near the plurality of apertures 302 may be between about 5 μm and about 10 μm.

As shown in FIG. 3A, in one embodiment, a height $\Phi_2$ of the sidewalls 306 may be between about 40 μm and about 80 μm, such as about 60 μm, 65 μm, etc. In another embodiment, a width $\Phi_1$ of the cavity 304 may be between about 50 μm and 80 μm, such as about 60 μm, 65 μm, etc. In preferred embodiments, the height $\Phi_2$ of the sidewalls 306 may correspond to the width $\Phi_1$ of the cavity 304. In one or more embodiments, the pitch $\Phi_5$ (a distance measured between apertures) of one or more of the apertures 302 may be between about 2 μm to 20 μm, or about 4 μm to 10 μm, or any value or range in between. In some embodiments, the selection of the pitch impacts or effects flow rate, and/or mechanical strength of the aperture plate. In some embodiments, selection of pitch is a function of mechanical considerations, such as vibration frequency.

Referring now to FIG. 3B, a top view of the aperture plate 300 is shown, according to one embodiment, taken from Line 3B in FIG. 3A. Referring again to FIG. 3B, an aperture pattern is shown having a star shape, but any shape or configuration may be used as desired, such as circular, square, triangular, or free-form, etc. The process of the present invention permits forming into the aperture plate 300 a significantly larger number of apertures 302 than which may be formed into an aperture plate according to the prior art. This is due to the process described herein according to various embodiments which allows more freedom and precision in defining aperture patterns, aperture density, aperture shape and aperture size as desired to achieve the desired liquid delivery results. Moreover, embodiments described herein may make use of a greater percentage of an aperture plate area, because the aperture size is not dependent upon an aperture plate thickness. In other words, the thickness is decoupled from the aperture size, in contrast to aperture plates produced through prior art electroforming, in which the thickness of the aperture plate is interrelated to the size of the apertures. Therefore, more apertures 302 per unit of aperture plate area are possible, with a potential benefit of greater throughput while maintaining control of particle size and/or particle size distribution. In some embodiments, the number of apertures 302 may range from about 1 aperture to about 1000 apertures per $mm^2$. For a typically-sized aperture plate (i.e., 20 $mm^2$) for pulmonary delivery of a nebulized liquid drug, the number of apertures may range from about 50 to about 25,000, or about 300 to about 10,000, or any number range or value therebetween. FIG. 3B illustrates a configuration wherein 10,000 or more apertures may be formed. In one embodiment of a nebulizer device, having about a 20 $mm^2$ aperture plate, apertures may number from 500 to 5,000, for example from 1,000 to 3,000, or any range or value therebetween. While there is no practical lower limit to the number of apertures (e.g., one is the minimum) which may be formed into an aperture plate, the process of the present invention permits a greatly increased number, such as 500 or 1,000 or more per $mm^2$.

In one or more embodiments, the aperture exit opening (also referred to as an outlet) may have a diameter in a range from about 0.5 μm to about 10 μm, and in some embodiments it may range from about 1 μm to about 6 μm, about 1 μm to about 4 μm, about 1 μm to about 3 μm in diameter, etc., or any range or value therebetween. A distribution of aperture sizes may range from any desired smallest size to any desired largest size, and there is no required standard deviation between aperture sizes, according to various embodiments. The process described above, in one embodiment, advantageously permits better control over aperture size than prior art processes, thus aperture plates may be reliably and repeatably produced with very small exit openings of the apertures, such as 0.5 μm, 0.4 μm, 0.3 μm, 0.2 μm, 0.1 μm, etc. In addition, according to embodiments presented herein, the process is capable of better control precision in achieving the desired aperture size, and consequently, a more tightly controlled range, i.e., a sharper distribution curve. It is to be noted, however, that embodiments presented herein also provide for an aperture plate wherein apertures may purposefully be formed to have sizes different from one another, such as a set of 3 μm apertures and a set of 1 μm apertures in the same aperture plate.

According to embodiments of the present invention, the diameter $\Phi_4$ of the apertures 302, the height $\Phi_2$ of the sidewalls 306, the thickness $\Phi_3$ of the first material 308 near the plurality of apertures 302, the width $\Phi_1$ of the cavity 304, and/or the pitch $\Phi_5$ may be independently controlled, such as to provide a desired flow rate, droplet size and droplet size distribution, when aerosolizing a liquid through the apertures 302.

According to some embodiments, the first material 308 and/or the second material 310 may include any suitable material, such as at least one of Ni, Co, Pd, Pt, alloys thereof, and mixtures thereof, among other suitable materials. A suitable material may be any electroplatable material, and in some further embodiments, the material chosen may have a resistance to chemical properties of a liquid to be aerosolized with the aperture plate 300.

Figure 4A:
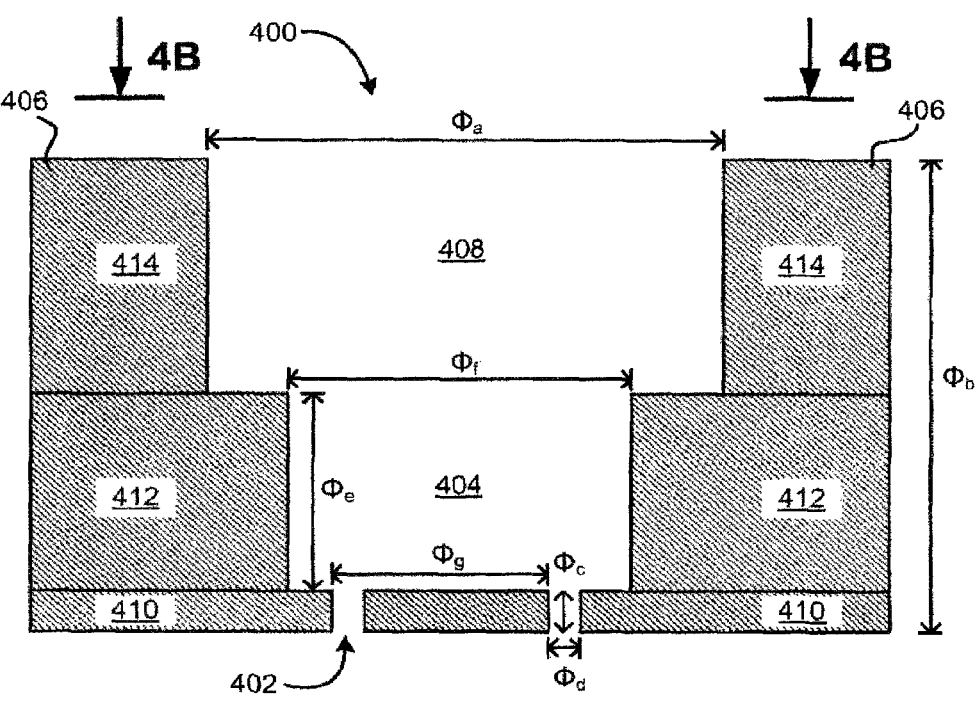
FIGS. 4A-4B show a cross-sectional view and a top view, respectively, of an aperture plate, according to one embodiment.
Figure 4B:
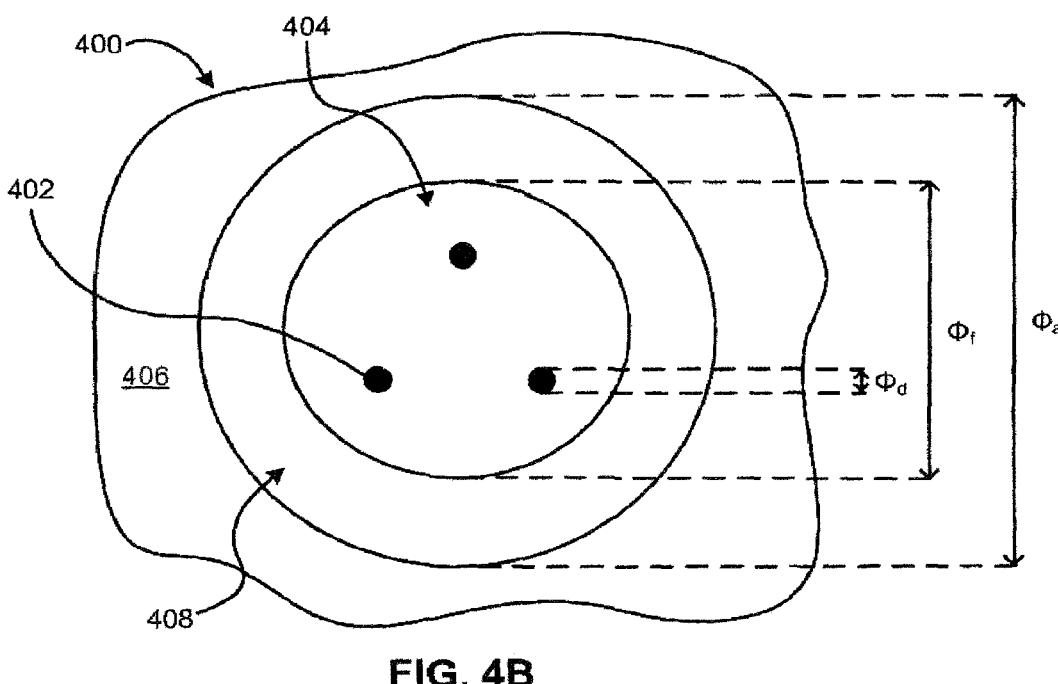

Now referring to FIGS. 4A-4B, a cross-sectional view and top view of an aperture plate 400 formed through a photolithography process are shown according to one embodiment. As can be seen in FIG. 4A, the aperture plate 400 includes a plurality of apertures 402, a first cavity 404, a second cavity 408, and sidewalls 406. The aperture plate 400 may be used for aerosolizing a liquid, according to preferred embodiments.

The aperture plate 400 includes a first material having a plurality of apertures 402 therein. The first material 410 is a layer having a thickness $\Phi_c$ the same as a height of the apertures 402. The first material 410 has a characteristic of being formed through a photolithography process, such as smooth surfaces, uniform growth, etc., as described previously. The aperture plate 400 also includes a second material 412 (which may be the same material or a different material than the first material 410) which is positioned directly or indirectly above the first material 410, the second material 412 having a first cavity 404 above the plurality of apertures 402 in the first material 410. The second material 412 is a layer having a thickness the same as a depth $\Phi_e$ of the first cavity 404. The second material 412 also has a characteristic of being formed through a photolithography process as described previously, which results in one or more beneficial properties of smooth surfaces, well controlled diameters ($\Phi_a$, $\Phi_d$, $\Phi_f$) and pitch ($\Phi_g$), uniform dimensions, etc.

The aperture plate 400 also includes a third material 414 having a second cavity 408, the third material 414 being positioned above the second material 412 such that the cavities 404 and 408 are positioned above one another. The third material 414 is a layer having a thickness which is the same as a depth of the second cavity 408, e.g., $\Phi_b$-($\Phi_c$+$\Phi_e$). The third material 414 has a characteristic of being formed through a photolithography process as described previously, the second cavity 408 is above the first cavity 404, and an internal diameter $\Phi_a$ of the second cavity 408 is greater than an internal diameter $\Phi_f$ of the first cavity 404.

In one approach, each of the plurality of apertures 402 of the first material 410 may have a diameter $\Phi_d$ of between about 1 μm and about 5 μm. In another approach, a thickness $\Phi_c$ of the first material 410 near the plurality of apertures 402 may be between about 5 µm and about 10 µm, such as about 6 µm.

As shown in FIG. 4A, in one embodiment, a height $\Phi_b$ of the sidewalls 406 may be between about 40 µm and about 80 µm, such as about 60 µm, 65 µm, etc. In another embodiment, a width $\Phi_f$ of the first cavity 404 may be between about 20 µm and 30 µm, such as about 25 µm. In another embodiment, a depth $\Phi_e$ of the first cavity 404 may be between about 20 µm and 30 µm, such as about 25 µm. In preferred embodiments, the height $\Phi_b$ of the sidewalls 406 may correspond to the width $\Phi_f$ of the first cavity 404 and/or second cavity.

Referring now to FIG. 4B, a top view of the aperture plate 400 is shown, according to one embodiment, taken from Line 4B in FIG. 4A. Referring again to FIG. 4B, an aperture pattern is shown having three apertures 402, but any shape and any number of apertures 402 may be produced, as desired. According to preferred embodiments, the diameter $\Phi_d$ of the apertures 402, the height $\Phi_b$ of the sidewalls 406, the thickness $\Phi_c$ of the first material 410 near the plurality of apertures 402, the width $\Phi_a$ of the second cavity 408, the width $\Phi_f$ of the first cavity 404, and the pitch $\Phi_g$ may each be controlled independently of one another, such as to provide a desired flowrate and droplet size when aerosolizing a liquid through the apertures 402.

According to some embodiments, the first material 410, the second material 412, and/or the third material 414 may comprise any suitable material. In some embodiments, the materials may suitably be selected from the platinum metals group. In some embodiments, the materials comprise at least one of Ni, Co, Pd, Pt, alloys thereof, and mixtures thereof, among other suitable materials. The aperture plate 400 may be constructed of a high strength and/or a corrosion resistant material. As one example, the plate body (e.g., the first material 410, the second material 412, and/or the third material 414) may be constructed from palladium or a palladium nickel alloy. Palladium or a palladium nickel alloy are corrosion resistant to many corrosive materials, particularly solutions for treating respiratory diseases by inhalation therapy, such as an albuterol sulfate or an ipratroprium solution, which may be used in medical applications. In some embodiments, at least one of the first, second and/or third material have a low modulus of elasticity, and can result in a lower stress for a given oscillation amplitude. Other materials that may be used to construct the plate body include stainless steel, stainless steel alloys, gold, gold alloys, and the like. A suitable material may be any electroplatable material, and in some further embodiments, the material chosen may be inert to, and/or have a chemical resistance to, an aerosolized liquid to be used with the aperture plate 400.

The apertures of the aperture plates in any one embodiment may have an exit opening having a diameter anywhere within a range from about 0.5 µm to about 6 µm, to produce droplets that are about 0.5 µm to about 6 µm in size. In other embodiments, the aperture exit opening (also referred to as an outlet) may have a diameter of from about 1 µm to about 4 µm, about 1 µm to about 3 µm, etc., or any range or value therebetween, to produce droplets of about a corresponding size. Generally, droplet size is approximately equal to outlet size, however exiting droplets may form and become slightly larger or smaller, depending upon the characteristics, such as the surface tension and/or rheological properties, of the liquid being aerosolized. Exit opening is used herein to mean the opening from which the droplet emerges, and which may also be considered as downstream, or distal, to the liquid supply. This is contrasted with the inlet opening, also referred to as a liquid supply opening, which is the opening in contact with, or proximal to, the supply of liquid to be aerosolized. The liquid supply opening is thus larger in diameter and/or area than the exit opening. In some embodiments, the liquid supply opening may range in size from about 20 µm to about 200 µm in diameter including any range or value therebetween.

In one or more embodiments, the apertures may be formed (as shown, for example, in FIGS. 3B and/or 4B) to describe a series of concentric, stepped-down cylinders within the aperture plate (as viewed from the inlet opening to exit opening). In some embodiments, the apertures may be formed to describe within the aperture plate two concentric cylinders, as shown in FIG. 3B. In such embodiments, the liquid inlet opening may be from about 20 µm to about 100 µm in diameter, and the exit opening may be from about 0.5 µm to about 6 µm in diameter. In some embodiments, the exit opening diameter may be about 1% to about 10% of the inlet opening diameter. More particularly, in one or more embodiments, an inlet opening may comprise a diameter from about 50 µm to about 80 µm, and an exit opening may comprise a diameter of from about 1 µm to about 4 µm.

In one or more embodiments, apertures may be formed into the aperture plate as three concentric cylinders, as shown in FIG. 4B. According to one or more embodiments, three or more concentric cylinders may be used to form within the aperture plate to describe the aperture(s). In such embodiments, the apertures comprise a cylindrical inlet opening, one or more intermediate cylindrical openings, and one or more cylindrical exit openings formed into the aperture plate. These openings may have diameters comprising anywhere from about 50 µm to about 200 µm for the inlet, about 10 µm to about 40 µm for the intermediate opening, and about 1 µm to about 5 µm for the exit opening. In should be noted that the concentric cylinder arrangement of openings does not necessarily require that the openings be coaxial. In some embodiments, as illustrated for example, in FIGS. 3, a plurality (two or more) of exit openings may be formed within the diameter of the larger inlet opening. Thus, multiple apertures 302 (the exit openings) are typically formed within the area circumscribed by aperture 304 (the inlet opening). These exit openings may be formed in a variety of patterns, configurations, and positions relative to an axis of the larger opening. While generally a straight-sided aperture is obtained, some angle in the side walls of the aperture may occur due to light attenuation in the lithography process. This angle tends to be more pronounced as aperture size decreases. Generally, an angle of the side walls of a given aperture does not adversely impact droplet ejection performance, and may in some embodiments, be beneficial.

In some embodiments described herein, the apertures generally describe in the aperture plate an inverted ziggurat shape. In particular, when referring to the embodiment described by FIGS. 4, the ziggurat shape is notable. The ziggurat shape may be used to provide mechanical strength to the aperture plate, such that the aperture plate is capable of being used in a vibrating mesh type nebulizer and can withstand the forces exerted on the aperture plate due to the vibrating. The shape of the aperture plate (e.g., ziggurat shape) is not necessarily used to provide a particular size, or size distribution of the resulting droplets.

Conveniently, the aperture plates described herein according to various embodiments may be formed in a shape of a dome (although other configurations, such as planar and near-planar, are suitable) as described generally in U.S. Pat.

No. 5,758,637, previously incorporated by reference. Typically, the aperture plate will be vibrated at a frequency in a range from about 45 kHz to about 200 kHz when aerosolizing a liquid. Further, when aerosolizing a liquid, the liquid may be placed into contact with a rear surface of the aperture plate where the liquid adheres to the rear surface by surface tension forces. Upon vibration of the aperture plate, liquid droplets are ejected from the front surface as described generally in U.S. Pat. Nos. 5,164,740; 5,586,550, and 5,758,637, previously incorporated by reference.

Now referring to FIG. 6, a method 600 for manufacturing an aperture plate is shown according to one embodiment. The method 600 may be carried out in any desired environment, and may include more or fewer operations than those shown in FIG. 6, according to various embodiments.

In operation 602, a releasable seed layer is deposited above a substrate. The releasable seed layer may preferably comprise an etchable material, such as a metal, for example a conductive metal. In some embodiments, the metal is one or more of: Al, Cu, Si, Ni, Au, Ag, steel, Zn, Pd, Pt, etc., alloys thereof such as brass, stainless steel, etc., mixtures of the foregoing, and the like. In some embodiments, the releasable seed layer may comprise an etchable conductive material, such as conductive metals like Au, Ti, Cu, Ag, etc., and alloys thereof. Of course, any other material may be used for the releasable seed layer as would be understood by one of skill in the art upon reading the present descriptions.

In operation 604, a first patterned photolithography mask is applied above the releasable seed layer. The first patterned photolithography mask has a negative pattern to a desired aperture pattern.

The aperture size may be defined precisely through the patterns of the photolithography mask (photo dots) made through the photolithography process. As compared to prior art methods which use an electroforming process, the aperture is formed through a three-dimensional growth of plating materials.

In one approach, the first patterned photolithography mask may impart apertures to the first material having a diameter of between about 0.5 μm and about 6 μm.

In operation 606, a first material is electroplated above the exposed portions of the releasable seed layer and defined by the first mask. In one approach, the first material near the apertures may be formed to a thickness that is independent of a diameter of the apertures, such as between about 5 μm and about 10 μm, according to some embodiments.

Figure 5A:
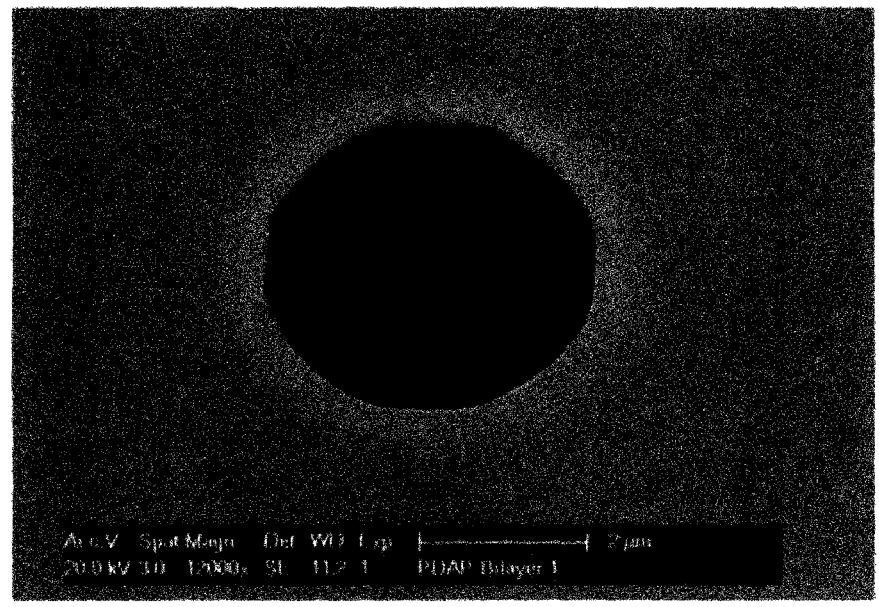
FIG. 5A shows a scanning electron microscope image of a top down view of an aperture plate, according to one embodiment.

The height of the first patterned photolithography mask and the thickness of the first material near the apertures are factors in determining the performance of the aperture plate after formation is complete. FIG. 5A shows a scanning electron microscope (SEM) image of a top down view of an internal side of an aperture from an aperture plate produced through methods described herein. As can be seen, the edges of this aperture are smooth and the shape is substantially uniform. The aperture shown in FIG. 5A was produced by plating the first material to a thickness that was less than the height of the first patterned photolithography mask, thereby ensuring that the material was deposited uniformly.

Figure 5B:
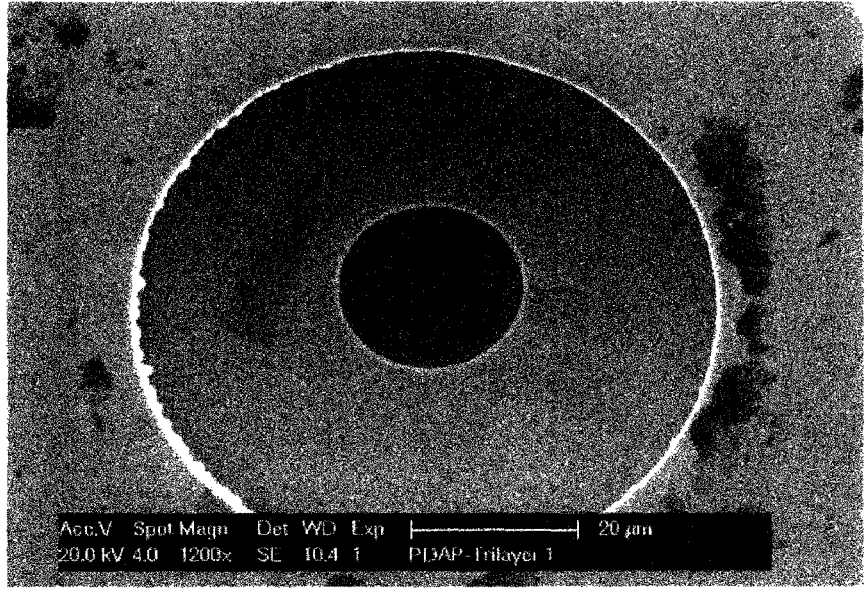
FIG. 5B shows a scanning electron microscope image of a top down view of an aperture plate, according to one embodiment.

Now referring to FIG. 5B, which is a SEM image of a top down view of an internal side of an aperture plate produced through methods described herein, some advantages of the methods are noticeable. The apertures in this aperture plate were produced in the same way as the aperture in FIG. 5A. The aperture plate shown in FIG. 5B has three planar surfaces, with each innermost surface being recessed from the next closest outermost surface, similar to the aperture plate shown in FIGS. 4A-4B. Referring again to FIG. 5B, it can be seen that the apertures are precisely controlled in placement and size, and the aperture plate has substantially vertical and substantially smooth walls. This precise manufacturing ability is an advantage to the methods described herein, according to various embodiments, when compared to conventional manufacturing methods, such as electroforming.

In some embodiments, the diameter of the apertures and the pitch of the apertures may be chosen (dependently or independently) such that the thickness of the first material near the apertures and a flow-rate of the aerosolized liquid through the apertures is controlled to achieve a desired value or range.

In another embodiment, a thickness of the first material near the apertures may be independent of a placement density of the apertures in the aperture pattern.

In operation 608, a second photolithography mask is applied above the first material. The second photolithography mask has a negative pattern to a first cavity.

In operation 610, a second material is electroplated above the exposed portions of the first material and defined by the second mask.

In one approach, the first material and the second material may be the same material. In another approach, the first material and the second material may comprise an electroplatable material having a resistance to an aerosolized liquid.

In operation 612, both masks are removed through any technique known in the art. In one embodiment, both masks are removed in a single step, e.g., they are removed at the same time.

In operation 614, the releasable seed layer is etched to release the plated materials. A preferred etching includes a wet etch process, among other methods of removing the release layer.

In one embodiment, the method 600 may include more operations, such as those described below.

In one optional operation, a third photolithography mask may be applied above the second material, the third photolithography mask having a negative pattern to a second cavity. This third photolithography mask may be applied prior to removing the first and second mask. Then, a third material may be electroplated above the exposed portions of the second material, and defined by the third mask. All masks may be removed after the completion of electroplating. The second cavity may be above the first cavity and an internal diameter of the second cavity may be greater than an internal diameter of the first cavity.

According to some embodiments, the first material, the second material, and/or the third material may comprise any suitable material. In some embodiments, the materials may suitably be selected from the platinum group. In some embodiments the materials comprise at least one of Ni, Co, Pd, Pt, and alloys thereof, among other suitable materials. The first material, the second material, and/or the third material may comprise a high strength and corrosion resistant material, in one embodiment. As one example, the first material, the second material, and/or the third material may comprise a palladium nickel alloy. Such an alloy is resistant to many corrosive materials, particularly solutions for treating respiratory diseases by inhalation therapy, such as an albuterol sulfate or ipratroprium solution, which may be used in medical applications. Further, the palladium nickel alloy has a low modulus of elasticity and therefore a lower stress for a given oscillation amplitude. Other materials that may be used for the first material, the second material, and/or the third material include palladium, palladium nickel alloys, stainless steel, stainless steel alloys, gold, gold alloys, and the like.

To enhance the rate of droplet production while maintaining the droplets within a specified size range, the apertures may be constructed to have a certain shape. In one or more embodiments, the apertures may be formed to describe in the aperture plate a ziggurat shape. Using this approach, aperture plates may be formed as a series of concentric, stepped down cylinders (as viewed from the inlet side to exit opening). In some embodiments, the aperture plates may be formed as two concentric cylinders. In such embodiments, the liquid inlet may be from about 50 μm to about 100 μm, and the exit opening may be from about 0.5 μm to about 6 μm. More particularly, in one embodiment, an inlet opening may comprise a diameter from about 60 μm to about 80 μm, and an exit opening may comprise a diameter from about 1 μm to about 4 μm.

According to one or more embodiments, aperture plates may be formed as three or more concentric cylinders. In such embodiments, there is an inlet cylinder, one or more intermediate cylinders, and an exit plate having outlets formed therein. In some embodiments, the exit opening diameter for the outlets formed therein may be about 1% to about 50% of the inlet opening diameter. In some embodiments, the next smaller opening diameter may be about 10% to about 30% of the next larger opening diameter. For example, the diameters may comprise anywhere from about 50 μm to about 100 μm for the inlet, about 10 μm to about 30 μm for the intermediate, and about 1 μm to about 5 μm for the exit. In any of the foregoing, the apertures describe in the aperture plate an inverted ziggurat shape. Such a shape provides for a robust aperture plate, and may provide flow rate benefits, such as increased flow rate while maintaining droplet size. In this way, the aperture plate may find particular use with inhalation drug delivery applications. It is also to be noted that the aperture walls are described as generally straight-sided, that is, the aperture walls describe a section of a right circular cylinder geometric shape. In other word, the aperture walls are typically perpendicular to a plane of the aperture plate, or to a tangent to a dome-shaped aperture plate. In some embodiments, however, the aperture walls may possess some angle, and/or may even take on a conical cross-section.

According to one approach, the aperture plate may be formed in a fully automated process, which does not require manual stamping procedures.

Now referring to FIGS. 7A-7L, the method is described schematically.

Figures 7A, 7B, 7C, 7D, 7E:
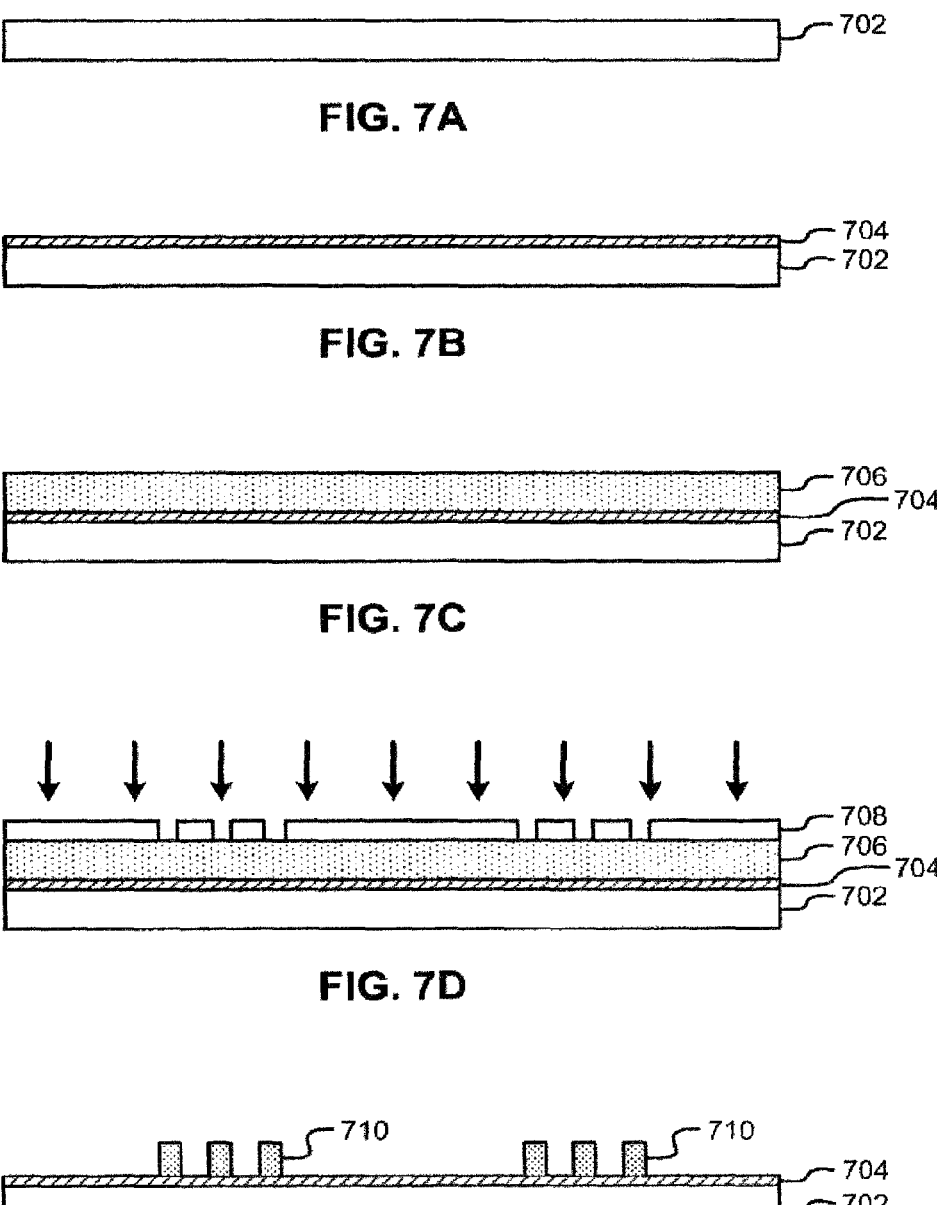

In FIGS. 7A-7B, a releasable seed layer 704 is deposited above a substrate 702. In preferred embodiments, the substrate 702 may comprise Si, and the releasable seed layer 704 may include any etchable conductive metal.

In FIGS. 7C-7E, a first patterned photolithography mask 710 is applied above the releasable seed layer 704. The first patterned photolithography mask 710 has a negative pattern to a desired aperture pattern, and may be formed by spin coating photoresist 706, applying a photomask 708 having a desired pattern to expose removed portions of the photoresist 706, and dissolving the exposed portions through any method known in the art, such as by use of a developer known in the art, thusly creating the first mask 710.

In FIG. 7F, a first material 712 is electroplated above the exposed portions of the releasable seed layer 704 and the patterns are defined by the first mask.

In FIGS. 7G-7I, a second photolithography mask 714 is applied above the first material 712. The second photolithography mask 714 has a negative pattern to a first cavity. The second photolithography mask 714 may be formed by spin coating photoresist 716, applying a photomask 718 having a desired pattern, exposing removed portions of the photoresist 716, and dissolving the exposed portions through any method known in the art, such as by use of a developer known in the art, thusly producing the second mask 714.

Figure 7J:
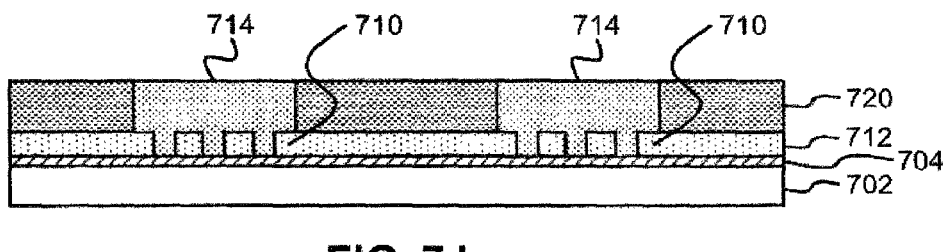
Figure 7K:
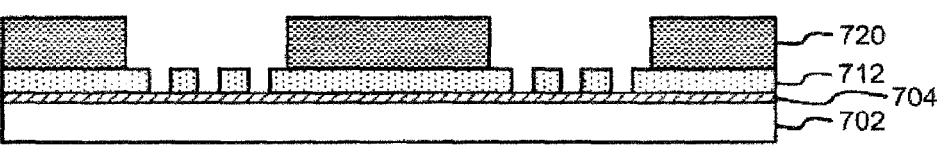
Figure 7L:
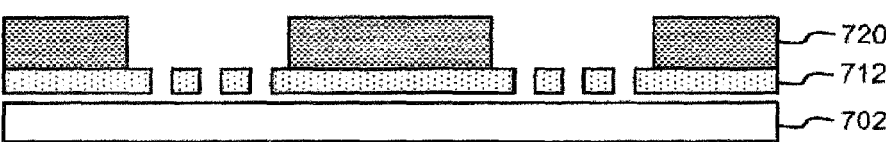

In FIG. 7J, a second material 720 is electroplated above the exposed portions of the first material 712 and the patterns are defined by the second mask. Then, the second mask 714 and the first mask 710 are removed through any technique known in the art, resulting in a structure as shown in FIG. 7K. Then, the releasable seed layer 704 is etched to release both the first material 712 and the second material 714, resulting in a structure as shown in FIG. 7L. A preferred etching includes a wet etch process. Other etching processes which may be suitable methods of removing the release layer include plasma etching and photochemical etching.

In preferred embodiments, the first material and the second material may form an aperture plate for use in aerosolizing a liquid in a vibrating mesh nebulizer. In these embodiments, the photo-defined approach permits control of flowrate independently of the droplet size because the aperture size and aperture pattern density may be independently controlled.

For example, the flowrate of a liquid aerosol generator is expected to be proportional to total aperture numbers (which when combined with the size of each aperture results in total aperture area). This is another significant advantage over the prior art where the aperture pattern density is limited by a required plating thickness. As a result, the methods disclosed herein of making aperture plates may provide a parametrically controlled aperture plate to meet desired specifications for delivery of a wide variety of liquid drug formulations.

According to one embodiment, an aperture plate produced through methods described herein may include apertures of various sizes, various domains, various shapes, various profiles, various geometries, etc. For example, an aperture plate may comprise one or more domains comprising a plurality of apertures arranged in a circular pattern, together with one or more domains comprising a plurality of apertures arranged in a non-circular, such as elliptical, triangular, or quadrilateral pattern. The apertures in the different domains may have varying or identical areas, such as varying diameters of between about 1 μm to about 5 μm.

The apertures further may comprise an even dispersion about the area of the aperture plate, an uneven dispersion, or may be both evenly and unevenly dispersed, such as in different domains. In another embodiment, an aperture plate may include apertures having a first domain in an inner portion and apertures having a second domain in an outer portion. Moreover, the photolithographic process described herein allows production of the aperture plate itself in varying patterns or geometries. Thus, aperture plates can be readily formed to be circular, elliptical, square and/or star-shaped, for example. Tabs or projections may be formed onto the aperture plate to assist in manufacturing a nebulizer therewith, in some embodiments. Of course, any other arrangement of apertures, aperture sizes, aperture domains, aperture profiles, etc., may be produced using the methods described herein, as would be understood by one of skill in the art upon reading the present descriptions.

The methods disclosed herein do not require a stringent alignment tolerance between layers because of the displacement of the two or more layers provides a good alignment margin. Additional advantages over the electroforming process of making aperture plates include that the photo-defined aperture size is not related to the plating thickness. Therefore, using a photo-defined process enables improved process control and a potential for improved manufacturing yield. The dependence of aperture size on plating thickness has been a significant factor in yield loss for conventional electroforming processes, which can now be avoided using techniques described herein. Also, multi-layer processes can be used to achieve a final desired aperture plate geometry, which was not possible using conventional aperture plate formation techniques.

Aperture plates have been built using the processes described herein, and aerosol testing data from these aperture plates appear below in Table 1 for performance comparison. Table 1 shows test results of three photo-defined aperture plates according to embodiments herein and three electroformed aperture plates according to the prior art.

TABLE 1

| TCAG # | Type | VMD (μm) | GSD | Span |
|--------|------|----------|-----|------|
| P35 | Photo-defined | 2.6 | 1.5 | 1.3 |
| P42 | Photo-defined | 2.5 | 1.5 | 1.3 |
| P43 | Photo-defined | 2.2 | 1.5 | 1.2 |
| Avg | Photo-defined | 2.4 | 1.5 | 1.3 |
| F007 | Electroforming | 4.2 | 1.9 | 1.7 |
| F038 | Electroforming | 4.0 | 1.8 | 1.7 |
| F044 | Electroforming | 4.4 | 1.8 | 1.7 |
| Avg | Electroforming | 4.2 | 1.8 | 1.7 |

In Table 1, TCAG indicates which sample of a tube core aerosol generator was tested, VMD indicates a volume median diameter which is determined based on the size of the droplets exiting the aperture plate, GSD indicates a geometric standard distribution and is the calculation of ($D_{84}/D_{50}$), and Span indicates the span of the calculation of ($D_{90}$-$D_{10}$)/$D_{50}$, where D is a droplet size at the percentile (as indicated by the subscript numbering) of the droplet size distribution which was measured by light scattering technology, such as a Malvern light scattering instrument. For example, for a photo-defined unit P35, the light scattering method measures $D_{10}$=1.414 μm, $D_{50}$=2.607 μm, $D_{84}$=4.038 μm, $D_{90}$=4.844 μm, so the GSD=$D_{84}/D_{50}$=1.549. For an electroformed unit F007, the light scattering method measures $D_{10}$=1.585 μm, $D_{50}$=4.245 μm, $D_{84}$=8.052 μm, $D_{90}$=8.935 μm, so the GSD=$D_{84}/D_{50}$=1.897.

By way of comparison, the droplet size distribution for photo-defined units is 79% narrower than that for electroformed ones when assuming the same value of $D_{50}$, which indicates better controlled droplet size of aerosolized medicine and more effective dosage delivered into the lung.

As can be seen from Table 1, the aperture plates produced through methods described herein (P35, P42, P43) have a smaller GSD than conventionally produced (prior art) aperture plates (F007, F038, F044). A smaller droplet size (near 1-2 μm) is considered very desirable to target deep lung delivery. A smaller GSD corresponds to a narrower distribution of droplet size produced by the aperture plate, which is a desirable characteristic for effective targeted delivery into the lung.

The units tested and tabulated in Table 1 are "hybrid" aperture plates. Here, the "hybrid" means that the apertures and aperture plate geometry are defined through photolithographic process but aperture plates are made on stainless steel substrates and harvested from the substrate instead of Si or some other substrate material.

The first prototype made through methods described herein shows promising results. It delivers up to a 1.2 mL/min flowrate at a median droplet size of 3.3 μm. For comparison, a typical electroformed aperture plate device delivers only 0.3 mL/min flowrate at a larger median droplet size of 4.6 μm. The photo-defined aperture plate is also capable of delivering an even smaller droplet size, about 2.7 μm at a flow rate of 0.4 mL/min. This is a significant improvement over an aperture plate manufactured using a prior art electroforming process. Marked improvement is achieved in delivery of smaller droplet sizes in VMD and in achieving a narrower size distribution, e.g., GSD and Span for photo-defined aperture plates vs. electroformed ones. A further improvement in aperture size, aperture shape, and/or size distribution control is expected with fully photo-defined processes, in which stainless steel substrates are replaced with high quality Si substrates. Thus, a more precisely controlled aperture size may be achieved from the photolithographic process of the present invention than are shown in the results of Table 1.

Aperture plates may be constructed so that a volume of liquid in a range from about 4 μL to about 30 μL may be aerosolized within a time duration of less than about one second by using an aperture plate having about 1000 apertures, according to some embodiments. Further, the droplet size and droplet size distribution resulting from aerosolization through the aperture plate of the present invention may result in a respirable fraction (e.g. that fraction of droplets which reach the deep lung) that is greater than about 40% or 50% or 60%, 70% or 80% or 90% or 95% or 98% or 99% in many embodiments. In one or more embodiments, this respirable fraction is achieved by using the aperture plate of the present invention with a piezo-actuated, vibrating mesh type nebulizer, such as those described in U.S. Pat. Nos. 5,164,740, 5,586,550, and 5,758,637, previously incorporated by reference. In this way, a medicament may be aerosolized and then efficiently inhaled by a patient.

Figure 8A:
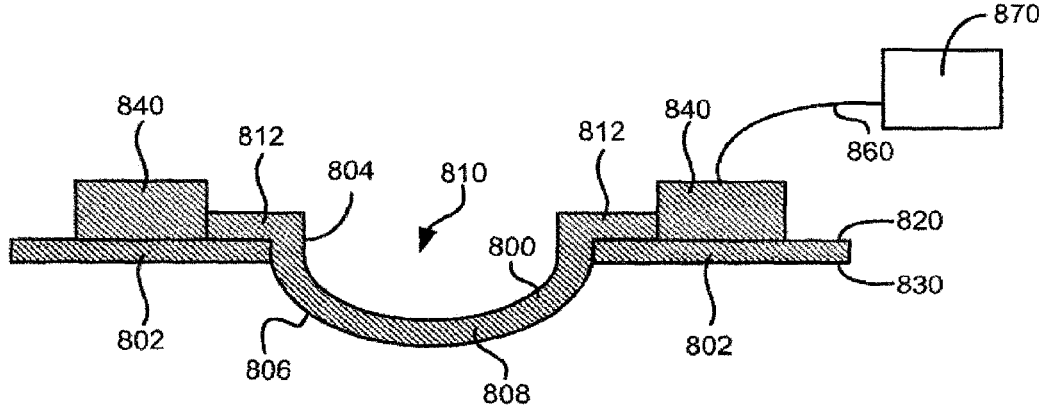
FIG. 8A is a schematic cross-sectional representation of a nebulizer including an aperture plate, according to one embodiment.
Figure 8B:
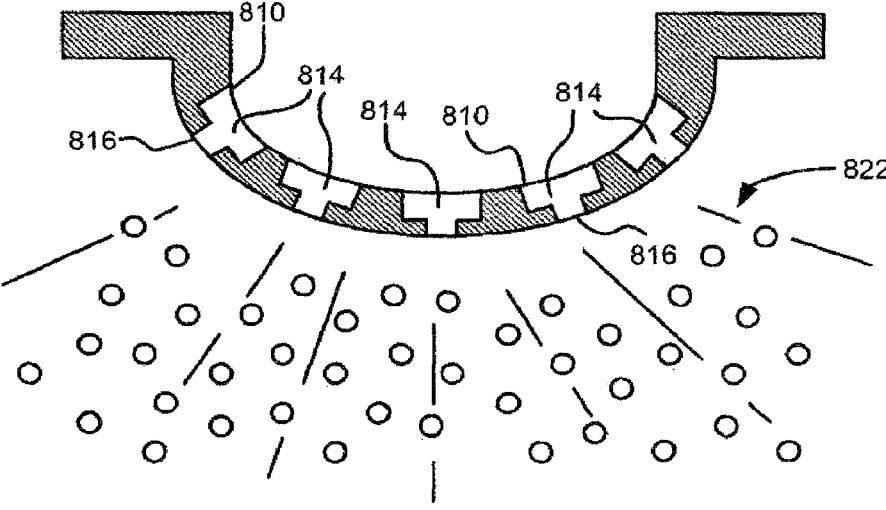
FIG. 8B is a schematic cutaway cross-section detail of the nebulizer shown in FIG. 8A, according to one embodiment.

Now referring to FIGS. 8A-8B, a vibrating mesh type nebulizer is shown according to one embodiment. As shown in FIG. 8A, an aperture plate 800 may be configured to have a curvature, as in a dome shape, which may be spherical, parabolic or any other curvature. Of course, in other embodiments, the aperture plate 800 may be substantially planar, and is not limited to the arrangement shown in FIGS. 8A-8B. The aperture plate 800 may be formed to have a dome portion 808 over its majority, and this may be concentric with the center of the aperture plate 800, thus leaving a portion of the aperture plate 800 that is a substantially planar peripheral ring portion 812. The aperture plate 800 may have a first face 804 and a second face 806. As shown in FIG. 8B, the aperture plate 800 may also have a plurality of apertures 814 therethrough. The first face 804 may comprise a concave side of the dome portion 808 and the second face 806 may comprise a convex side of the dome portion 808 of the aperture plate 800. The apertures 814 may be tapered to have a wide portion at the inlet 810 at the first face 804 and a narrow portion at the outlet 816 at the second face 806 of the aperture plate 800, or may be substantially straight from inlet 810 to outlet 816.

Typically, a liquid is placed at the first face 804 (also referred to as the liquid supply side) of the aperture plate 800, where it can be drawn into the inlet 810 of the apertures 814 and emitted as an aerosolized mist or cloud 822 from the outlet 816 of the apertures 814 at the second face 806 of the aperture plate 800.

The aperture plate 800 may be mounted on an aerosol actuator 802, which defines an aperture 810 therethrough. This may be done in such a manner that the dome portion 808 of the aperture plate 800 protrudes through the aperture 810 of the aerosol actuator 802 and the substantially planar peripheral ring portion 812 on the second face 806 of the aperture plate 800 abuts a first face 820 of the aerosol actuator 802. In another embodiment where the aperture plate 800 is substantially planar, the portion of the aperture plate 800 where the apertures 814 are positioned may be placed in the aperture 810 of the aerosol actuator 802. A vibratory element 840 may be provided, and may be mounted on the first face 820 of the aerosol actuator 802, or alternatively may be mounted on an opposing second face 830 of the aerosol actuator 802. The aperture plate 800 may be vibrated in such a manner as to draw liquid through the apertures 814 of the aperture plate 800 from the first face 804 to the second face 806, where the liquid is expelled from the apertures 814 as a nebulized mist.

In some approaches, the aperture plate 800 may be vibrated by a vibratory element 840, which may be a piezoelectric element in preferred embodiments. The vibratory element 840 may be mounted to the aerosol actuator 802, such that vibration of the vibratory element 840 may be mechanically transferred through the aerosol actuator 802 to the aperture plate 800. The vibratory element 840 may be annular, and may surround the aperture 810 of the aerosol actuator 802, for example, in a coaxial arrangement.

In some embodiments, a circuitry 860 may provide power from a power source. The circuitry 860 may include a switch that may be operable to vibrate the vibratory element 840 and thus the aperture plate 800, and aerosolization performed in this manner may be achieved within milliseconds of operation of the switch. The circuitry 860 may include a controller 870, for example, a microprocessor, field programmable gate array (FPGA), application specific integrated circuit (ASIC), etc., that may provide power to the vibratory element 840 to produce aerosolized liquid from the aperture plate 800 within milliseconds or fractions of milliseconds of a signal to do so.

In some cases, the aperture plates described herein may be used in non-vibratory applications. For example, the aperture plates may be used as a non-vibrating nozzle where liquid is forced through the apertures. As one example, the aperture plates may be used with ink jet printers that use thermal or piezoelectric energy to force the liquid through the nozzles. The aperture plates described herein according to various embodiments may be advantageous when used as non-vibrating nozzles with ink jet printers because of their corrosive-resistant construction and potentially finer aperture size. The aperture plates of the present invention may be suitable for other fluid delivery applications, such as non-drug delivery medical applications, fuel injection, precise liquid deposition, and other applications where aerosolization is useful, and in particular where a benefit is realized from a combination of high throughput and small, precise droplet (particle) size. In many applications, the method of manufacturing apertures, as described herein according to various embodiments may afford cost and/or efficiency benefits even if precise droplet size control is not an important aspect of the produced aperture plate.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:
1. An aperture plate for use in aerosolizing a liquid in a nebulizer, comprising:

a first layer formed through a photolithography process and including a first thickness, the first layer defining a first plurality of apertures; and
a second layer formed through a photolithography process and including a second thickness, the second layer positioned above the first layer and defining a second plurality of apertures, wherein a first aperture from the first plurality of apertures and a second aperture from the second plurality of apertures form two stepped-down cylinders, and wherein the second thickness is greater than the first thickness.
2. The aperture plate of claim 1, wherein the two stepped-down cylinders are coaxial.
3. The aperture plate of claim 1, wherein the two stepped-down cylinders are concentric.
4. The aperture plate of claim 1, wherein the first aperture forms an outlet and the second aperture forms an inlet.
5. The aperture plate of claim 4, wherein the outlet includes a diameter between 1 μm and 5 μm and the inlet includes a diameter between 50 μm and 100 μm.
6. The aperture plate of claim 1, further comprising a third layer formed through a photolithography process, the third layer positioned above the second layer and defining a third plurality of apertures, wherein the first aperture from the first plurality of apertures, the second aperture from the second plurality of apertures, and a third aperture from the third plurality of apertures form three stepped-down cylinders.
7. The aperture plate of claim 1, wherein the first layer and the second layer comprise the same material.
8. The aperture plate of claim 7, wherein the material includes palladium or nickel.
9. The aperture plate of claim 1, wherein the first layer comprises a first material and the second layer comprises a second material different than the first material.
10. An aperture plate for use in aerosolizing a liquid in a nebulizer, comprising:
a first layer formed through a photolithography process, the first layer defining a first plurality of apertures;
a second layer formed through a photolithography process, the second layer positioned above the first layer and defining a second plurality of apertures; and
a third layer formed through a photolithography process, the third layer positioned above the second layer and defining a third plurality of apertures, wherein a first aperture from the first plurality of apertures, a second aperture from the second plurality of apertures, and a third aperture from the third plurality of apertures form three stepped-down cylinders.
11. The aperture plate of claim 10, wherein the first aperture forms an outlet cylinder, the second aperture forms an intermediate cylinder, and the third aperture forms an inlet cylinder.
12. The aperture plate of claim 11, wherein the outlet cylinder includes a diameter between 1 μm and 5 μm, the intermediate cylinder includes a diameter between 10 μm and 30 μm, and the inlet cylinder includes a diameter between 50 μm and 100 μm.
13. The aperture plate of claim 10, wherein the first layer, the second layer, and the third layer comprise the same material.
14. The aperture plate of claim 10, wherein the first layer comprises a first material, the second layer comprises a second material different than the first material, and the third layer comprises a third material different than the first material and the second material.
15. A method for manufacturing an aperture plate for aerosolizing a liquid in a nebulizer, the method comprising:

applying a first patterned photolithography mask above the releasable seed layer;

electroplating a first material above exposed portions of the releasable seed layer and between portions of the first patterned photolithography mask;

applying a second patterned photolithography mask above the first material;

electroplating a second material above exposed portions of the first material and between portions of the second patterned photolithography mask;

removing the first patterned photolithography mask to form a first layer defining a first plurality of apertures;

removing the second patterned photolithography mask to form a second layer defining a second plurality of apertures, wherein a first aperture from the first plurality of apertures and a second aperture from the second plurality of apertures form two stepped-down cylinders; and etching the releasable seed layer to release the first material and the second material.

16. The method of claim 15, wherein the two stepped-down cylinders are coaxial.

17. The method of claim 15, wherein the two stepped-down cylinders are concentric.

18. The method of claim 15, wherein the first aperture forms an outlet and the second aperture forms an inlet.

19. The method of claim 15, wherein the first layer includes a first thickness, wherein the second layer includes a second thickness, and wherein the second thickness is greater than the first thickness.

* * * * *